United States Patent [19]
Adachi et al.

[11] Patent Number: 5,445,157
[45] Date of Patent: Aug. 29, 1995

[54] THERMOGRAPHIC ENDOSCOPE

[75] Inventors: Rensuke Adachi; Hiroshi Sone; Chinari Tanaka, all of Tokyo, Japan

[73] Assignee: Asahi Kogaku Kogyo Kabushiki Kaisha, Tokyo, Japan

[21] Appl. No.: 18,529

[22] Filed: Feb. 17, 1993

[30] Foreign Application Priority Data

Feb. 20, 1992 [JP] Japan .................. 4-033009

[51] Int. Cl.$^6$ ............................................. A61B 6/00
[52] U.S. Cl. ...................... 128/664; 128/633; 128/634; 128/665; 128/736; 600/109
[58] Field of Search ............... 128/664, 665, 633, 634, 128/4.6, 736; 606/2, 14, 15, 46; 607/104, 105, 113; 356/51

[56] References Cited

U.S. PATENT DOCUMENTS

| Re. 34,411 | 10/1993 | Nishida et al. | 128/6 |
|---|---|---|---|
| 3,877,463 | 4/1975 | Cary et al. | 128/736 |
| 3,970,074 | 7/1976 | Mogos et al. | 128/736 |
| 4,021,663 | 5/1977 | Takahashi . | |
| 4,445,516 | 5/1984 | Wollnik et al. | 128/736 |
| 4,557,272 | 12/1985 | Carr | 128/736 |
| 4,638,800 | 1/1987 | Michel | 606/10 |
| 4,768,513 | 9/1988 | Suzuki | 128/665 |
| 4,971,034 | 11/1990 | Doi et al. . | |
| 4,995,398 | 2/1991 | Turnidge | 128/736 X |
| 4,998,527 | 3/1991 | Meyer | 128/4 |
| 5,056,525 | 10/1991 | Hafezi | 128/736 X |
| 5,070,874 | 12/1991 | Barnes et al. | 128/664 |
| 5,074,862 | 12/1991 | Rausis | 606/14 |
| 5,078,150 | 1/1992 | Hara et al. | 128/664 |
| 5,161,531 | 11/1992 | Parsons et al. | 128/665 |
| 5,187,572 | 2/1993 | Nakamura et al. | 128/6 |
| 5,197,470 | 3/1993 | Helfer et al. | 128/664 |
| 5,293,872 | 3/1994 | Alfano et al. | 128/664 |

FOREIGN PATENT DOCUMENTS

| 1104239 | 4/1989 | Japan . | |
| 0023831 | 1/1991 | Japan | 128/6 |

OTHER PUBLICATIONS

Kimura et al., Use of Gas Jet Appositional Pressurization in Edoscopic Laser Photocoagulation, IEEE Tran. Bio. Eng., vol. 25 No. 3, May 1978.

Primary Examiner—Lee S. Cohen
Assistant Examiner—Brian L. Casler
Attorney, Agent, or Firm—Sandler, Greenblum & Bernstein

[57] ABSTRACT

A thermographic endoscope having an insert part that is inserted into a body cavity. The thermographic endoscope includes an infrared image forming device disposed in the distal end of the insert part so as to form an infrared image of a part under inspection, and a device for transmitting the infrared image formed by the infrared image forming device to the outside of the insert part. The thermographic endoscope further includes a device for converting the infrared image, which is transmitted by the infrared image transmitting device, into a visible image and for displaying the visible image, and a device for injecting low-temperature gas outwardly from the distal end of the insert part of the endoscope.

11 Claims, 3 Drawing Sheets

THERMOGRAPHIC ENDOSCOPE

BACKGROUND OF THE INVENTION

The present disclosure relates to subject matter contained in Japanese Patent Application No. 4-33009 (filed on Feb. 20, 1992), which is expressly incorporated herein by reference in its entirety.

1. Field of the Invention

The present invention relates to a thermographic endoscope which is used to detect a temperature distribution in a part under inspection in a body cavity.

2. Description of the Prior Art

Medical endoscopes are widely used for various purposes, for example, detection of cancer. It is, however, extremely difficult to detect an early cancer, a malignant tumor under the mucous membrane, etc. by the naked eye.

However, since the temperature of abnormal cells such as cancer cells is a little higher than that of normal cells, an early cancer, a malignant tumor, etc. can be discovered by detecting a temperature distribution in the mucous membrane of the body cavity by using an endoscope. Attempts have already been made to effect such a detection by using a thermographic endoscope.

A typical thermographic endoscope, which is used for the above-described purposes, is arranged such that an infrared image that is formed in the distal end of the insert part of the endoscope is transmitted through, for example, an infrared image transmitting fiber bundle to the outside of the insert part of the endoscope, where the infrared image, that is, a temperature distribution, is visually displayed in the form of variations in color by using, for example, a thermovision.

However, the minimum temperature difference (resolving power) that can be detected with a thermovision through an infrared image transmitting fiber bundle is generally of the order of 1° C. Therefore, if the temperature difference between abnormal and normal cells is smaller than 1° C., the existence of abnormal cells cannot be detected.

SUMMARY OF THE INVENTION

An object of the present invention is to provide a thermographic endoscope, which is capable of detecting a temperature distribution in a part under inspection, and finding abnormal cells, even if the temperature difference between the normal and abnormal cells is small.

Other objects and advantages of the present invention will become apparent from the following detailed description of illustrated embodiments of the invention.

According to the present invention, there is provided a thermographic endoscope having an insert part that is inserted into a body cavity. The thermographic endoscope includes an infrared image forming device disposed in the distal end of the insert part so as to form an infrared image of a part under inspection, and a device for transmitting the infrared image formed by the infrared image forming device to the outside of the insert part. The thermographic endoscope further includes a device for converting the infrared image, which is transmitted by the infrared image transmitting device, into a visible image and for displaying the visible image, and a device for injecting low-temperature gas outwardly from the distal end of the insert part of the endoscope.

BRIEF DESCRIPTION OF THE DRAWINGS

The present invention may be more fully understood from the description of preferred embodiments of the invention set forth below, together with the accompanying drawings, in which.

DETAILED DESCRIPTION OF THE EMBODIMENTS

Embodiments of the present invention will be described below with reference to the accompanying drawings.

Figure 1:
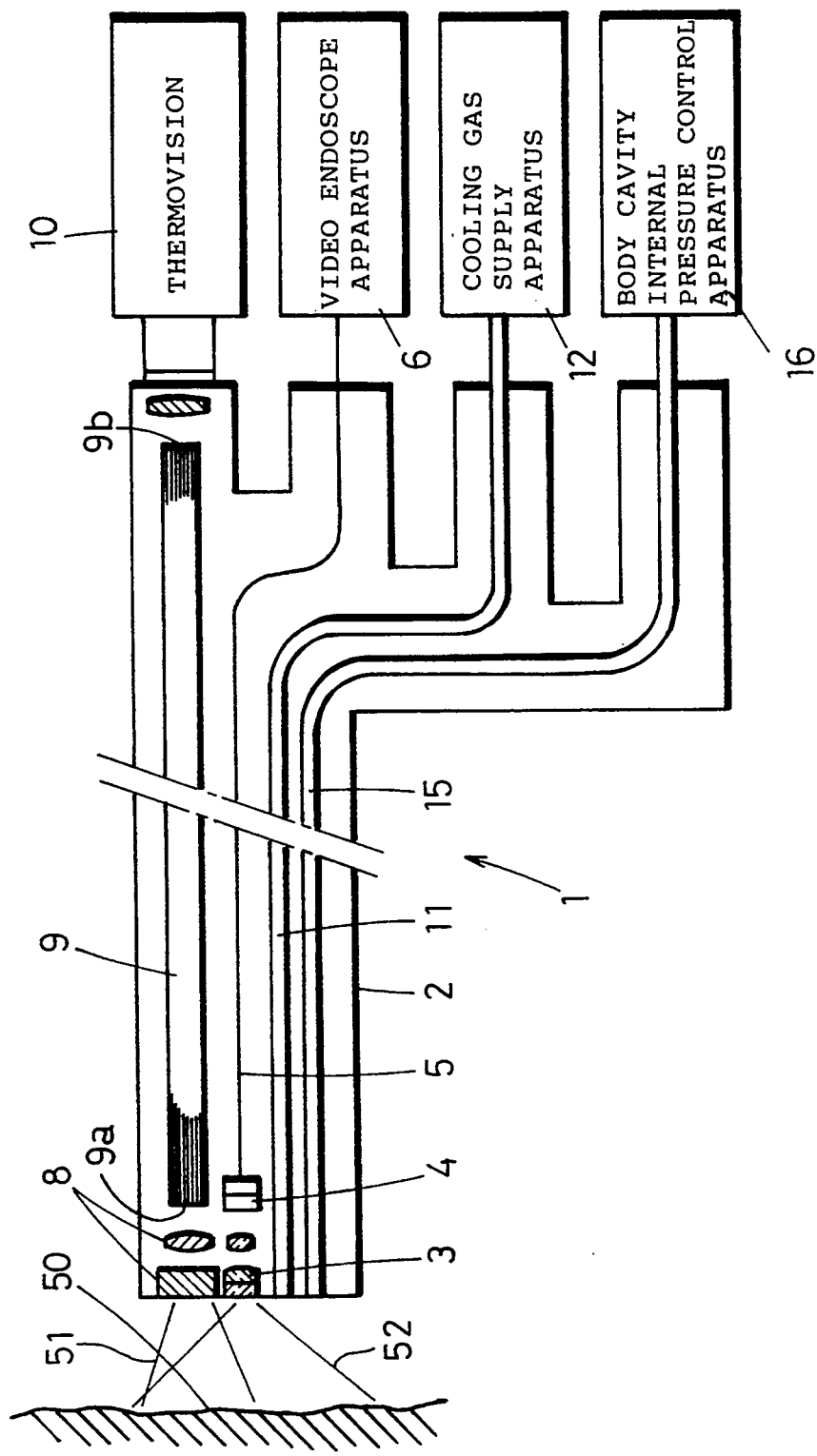
FIG. 1 shows the general arrangement of a first embodiment of the present invention.

Referring to FIG. 1, an endoscope 1 has a long, slender insert part 2 that is sheathed with a flexible tube. In the distal end of the insert part 2 is disposed an objective lens 3 for forming a visible image of a part 50 under inspection.

An optical image of the part 50 under inspection, which is formed by the visible image objective lens 3, is converted into an electric signal in a solid-state imaging device 4 and then led to the outside of the insert part 2 through a signal cable 5. Then, the optical image, which is now in the form of electric signal, is reproduced as a visible color image by a video endoscope apparatus 6 including a video controller, a monitor, etc. It should be noted that an image guide fiber bundle may also be employed as a means for transmitting a visible image.

An infrared objective lens 8 is disposed in the distal end of the insert part 2 in parallel to the visible image objective lens 3 so as to form an infrared image of the part 50 under inspection. The infrared objective lens 8 is made of an infrared transmitting material, for example, chalcogenide glass, fluoride glass, zinc selenide, germanium, or silicon.

An infrared image transmitting fiber bundle 9, which is formed by bundling up optical fibers that transmit infrared rays, is inserted into the insert part 2. To form the infrared image transmitting fiber bundle 9, it is preferable to use a bundle of chalcogenide-teflon clad optical fibers, each having a core made of chalcogenide glass, e.g., arsenic sulfide, and a cladding made of a polyfluoroethylene resin material, or a bundle of fluoride optical fibers so that when an indium antimonide detector, which detects infrared radiation in a medium infrared region ranging in wavelength from 3 $\mu$m to 5.5 $\mu$m, is used as an infrared detector of a thermovision 10 (described later), the loss in the wavelength range is minimized.

The entrance end face 9a of the fiber bundle 9 is disposed at a position where an image of the part 50 under inspection is formed by the infrared objective lens 8.

The exit end face 9b of the infrared image transmitting fiber bundle 9 is connected to a known thermovision 10 outside the insert part 2. Thus, an infrared image of the part 50 under inspection, that is, a temperature distribution, is visually displayed in the form of variations in color on a display, e.g., a CRT.

It should be noted that the viewing range 52 for the visible image is wider than the viewing range 51 for the infrared image, so that the infrared image viewing range 51 and its vicinities can be always clearly confirmed by the visible image.

A cooling gas supply pipe 11 extends through the insert part 2. The distal end of the cooling gas supply pipe 11 opens in the distal end face of the insert part 2, while the proximal end of the tube 11 is connected to a cooling gas supply apparatus 12 outside the insert part 2.

The cooling gas supply apparatus 12 cools and sends out a gas, e.g., air or carbon dioxide gas. Cooling gas at about 20° C., for example, is sent through the cooling gas supply pipe 11 into the body cavity that includes the part 50 under inspection and its vicinities.

The temperature of the cells in the part 50 under inspection and its vicinities is lowered by the cooling gas. However, the temperature of a region which is made up of abnormal cells, e.g., cancer cells, does not lower as much as that of the normal cell region does because a relatively large quantity of heat is given off by such an abnormal cell region. Consequently, the temperature difference between the abnormal and normal cell regions increases, and a distribution of abnormal cell regions is clearly displayed on the thermovision 10.

It should be noted that if the cooling gas is continuously sent into the body cavity, the pressure inside the body cavity will excessively rise, causing the patient pain. To avoid such a problem, a body cavity internal pressure control apparatus 16 is connected to the proximal end of a body cavity internal pressure control pipe 15 the distal end of which opens in the distal end face of the insert part 2, thereby maintaining the pressure inside the body cavity at a set level.

As the body cavity internal pressure control apparatus 16, an apparatus that is disclosed, for example, in Japanese Patent Application Laid-Open (KOKAI) No. 1-104239 (1989) may be employed.

Figure 2:
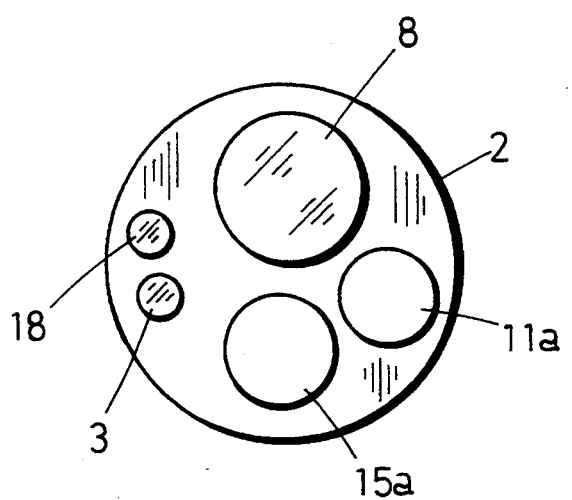
FIG. 2 is a front view showing the distal end of an insert part of the first embodiment of the present invention.

FIG. 2 is a front view of the distal end of the insert part 2. The exit end 18 of an illuminating light guide fiber bundle is disposed in side by side relation to the visible image objective lens 3, thereby allowing the part 50 under inspection to be illuminated with visible light. Reference numerals 11a and 15a denote the respective openings of the cooling gas supply pipe 11 and the body cavity internal pressure control pipe 15.

Figure 3:
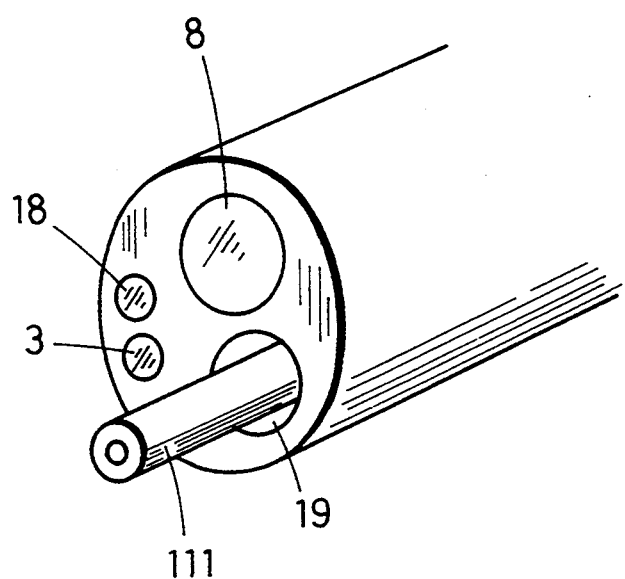
FIG. 3 is a perspective view showing the distal end of an insert part of a second embodiment of the present invention.

It should be noted that the present invention is not necessarily limited to the foregoing embodiment. For example, the temperature of the cooling gas may be set in the range of about 0° C. to 36° C. according to the particular circumstances. In addition, the arrangement may be such that a cooling gas supply pipe 111 is removably inserted into a forceps channel 19 that extends through the insert part 2 over the entire length thereof and opens at its distal end in the distal end face of the insert part 2, as shown in FIG. 3.

It is also possible to use a solid-state infrared imaging device and a processor therefor in place of the infrared image transmitting fiber bundle 9 and the thermovision 10.

According to the present invention, low-temperature gas is sent into a body cavity by the low-temperature gas injection device, thereby lowering the temperature of the cells in the body cavity including a part under inspection and its vicinities.

Since the temperature of an abnormal cell region, e.g., a cancer, does not lower as much as that of the normal cell region does because of a relatively large amount of heat given off by such an abnormal cell region, the temperature difference between the abnormal and normal cell regions increases.

Consequently, if there is an abnormal region in the part under inspection, the temperature difference between the abnormal and normal regions is magnified, so that the existence of the abnormal region can be surely detected.

While the invention has been described by reference to specific embodiments chosen for purposes of illustration, it should be apparent that numerous modifications could be made thereto by those skilled in the art without departing from the basic concept and scope of the invention.

We claim:

1. A thermographic/endoscope having an insert part that is inserted into a body cavity, said insert part having an outside and a distal end, said endoscope comprising:

infrared image forming means disposed in said distal end of said insert part so as to form an infrared image of a part under inspection;

means for transmitting the infrared image formed by said infrared image forming means to the outside of said insert part;

means for converting the infrared image, which is transmitted by said infrared image transmitting means, into a visible image and for displaying said visible image, said means for converting the infrared image being a thermovision that visually displays a temperature distribution indicating a temperature difference between normal and abnormal cells, the temperature difference being displayed in the form of variations in color on a display; and means for injecting a low temperature gas outwardly from the distal end of said insert part of said endoscope, said low temperature gas increasing the variations in color indicating the temperature difference between normal and abnormal cells on said display.

2. A thermographic endoscope according to claim 1, wherein said infrared image transmitting means is an infrared image transmitting fiber bundle formed by bundling optical fibers that transmit infrared rays.

3. A thermographic endoscope according to claim 1, wherein said low-temperature gas injection means cools a gas and sends said cooled gas from the outside of said insert part to the distal end of said insert part.

4. A thermographic endoscope according to claim 3 wherein said gas is air.

5. A thermographic endoscope according to claim 3 wherein said gas is carbon dioxide gas.

6. A thermographic endoscope according to claim 1, wherein said low-temperature gas injection means includes a gas supply pipe for passing said low-temperature gas, said gas supply pipe being inserted in said insert part.

7. A thermographic endoscope according to claim 1, wherein said low-temperature gas injection means includes a gas supply pipe for passing said low-temperature gas, said gas supply pipe being removably inserted into a forceps channel that extends through said insert part over an entire length of said insert part and opens at said distal end in a distal end face of said insert part.

8. A thermographic endoscope according to claim 1, further comprising means for observing a visible image of said part under inspection outside said insert part.

9. A thermographic endoscope according to claim 8, wherein said visible image observing means has a viewing range wider than a range of the image displayed by said means for converting the infrared image.

10. A thermographic endoscope according to claim 1, further comprising a body cavity internal pressure control apparatus, whereby pressure within the body cavity is maintained at a predetermined level.

11. A thermographic endoscope according to claim 10, wherein said body cavity internal pressure control apparatus is connected to a pressure control pipe, said pressure control pipe being open at said distal end of said insert part.

* * * * *

UNITED STATES PATENT AND TRADEMARK OFFICE
CERTIFICATE OF CORRECTION

PATENT NO. : 5,445,157
DATED : August 29, 1995
INVENTOR(S) : R. ADACHI et al.

It is certified that error appears in the above-indentified patent and that said Letters Patent is hereby corrected as shown below:

At column 4, line 15 (claim 1, line 1), change "thermographic/endoscope" to ---thermographic endoscope---.

Signed and Sealed this

Thirtieth Day of July, 1996

Attest:

BRUCE LEHMAN

*Attesting Officer*  *Commissioner of Patents and Trademarks*